US006657067B2

(12) United States Patent
Colborn et al.

(10) Patent No.: US 6,657,067 B2
(45) Date of Patent: *Dec. 2, 2003

(54) METHOD FOR THE MANUFACTURE OF CHLOROPHTHALIC ANHYDRIDE

(75) Inventors: Robert Edgar Colborn, Niskayuna, NY (US); David Bruce Hall, Ballston Lake, NY (US); Peter Koch, Frankfurt (DE); Gerald Oeckel, Frankfurt (DE)

(73) Assignee: General Electric Company, Pittsfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/063,112

(22) Filed: Mar. 22, 2002

(65) Prior Publication Data

US 2003/0181756 A1 Sep. 25, 2003

(51) Int. Cl.⁷ .................. C07D 493/02; C07D 209/48; C07C 51/16; C07C 51/255
(52) U.S. Cl. ................. 548/476; 562/416; 549/246
(58) Field of Search .............. 549/246; 562/416; 548/476

(56) References Cited

U.S. PATENT DOCUMENTS

| | | | |
|---|---|---|---|
| 2,245,528 A | 6/1941 | Loder | 260/524 |
| 2,415,800 A | 2/1947 | Rust | 260/524 |
| 2,445,528 A | 7/1948 | Keogh, Jr. | 30/41 |
| 2,833,816 A | 5/1958 | Saffer et al. | 260/524 |
| 2,883,816 A | 4/1959 | Kroll | 53/244 |
| 2,925,425 A | 2/1960 | Contois, Jr. et al. | 260/346.4 |
| 2,930,802 A | 3/1960 | Aries | 260/346.4 |
| 3,012,038 A | 12/1961 | O'Neill et al. | 260/295 |
| 3,086,991 A | 4/1963 | Keith et al. | 260/524 |
| 3,089,906 A | 5/1963 | Saffer et al. | 260/524 |
| 3,089,907 A | 5/1963 | Saffer et al. | 260/524 |
| 3,092,658 A | 6/1963 | Baldwin et al. | 260/524 |
| 3,161,658 A | 12/1964 | Meyer | 260/346.3 |
| 3,176,039 A | 3/1965 | Hay | 260/488 |
| 3,299,125 A | 1/1967 | Ichikawa | 260/524 |
| 3,334,135 A | 8/1967 | Ichikawa | 260/524 |
| 3,357,994 A | 12/1967 | Popp et al. | 260/327 |
| 3,402,184 A | 9/1968 | Berthoux et al. | 260/346.4 |
| 3,442,954 A | 5/1969 | Crocker et al. | 260/592 |
| 3,484,458 A | 12/1969 | Stein et al. | 260/346.4 |
| 3,549,695 A | 12/1970 | Bryant, Jr. et al. | 260/525 |
| 3,557,173 A | 1/1971 | Trevillyan | 260/439 |
| 3,578,706 A | 5/1971 | List et al. | 260/524 |
| 3,626,001 A | 12/1971 | Keith et al. | 260/574 |
| 3,655,521 A | 4/1972 | Gehrken et al. | 203/28 |
| 3,660,476 A | 5/1972 | Ichikawa et al. | 260/524 |
| 3,673,154 A | 6/1972 | Trevillyan | 260/524 |
| 3,681,399 A | 8/1972 | Barth | 260/346.4 |
| 3,721,708 A | 3/1973 | List et al. | 260/524 |
| 3,781,344 A | 12/1973 | Celle-St.-Cloud et al. | 260/524 |
| 3,839,436 A | 10/1974 | Longland, Jr. | 260/524 |
| 3,862,145 A | 1/1975 | Brennan et al. | 260/346.4 |
| 3,865,870 A | 2/1975 | Cronauer et al. | 260/524 |
| 3,865,871 A | 2/1975 | Horie et al. | 260/524 |
| 3,919,306 A | 11/1975 | Johnson et al. | 260/524 |
| 3,920,735 A | 11/1975 | Wampfler et al. | 260/524 |
| 3,950,409 A | 4/1976 | Yokota et al. | 260/524 |
| 3,970,696 A | 7/1976 | Shigeyasu et al. | 260/524 |
| 3,996,271 A | 12/1976 | Yokota et al. | 260/524 |
| 4,051,178 A | 9/1977 | Kimura et al. | 260/524 |
| 4,053,506 A | 10/1977 | Park et al. | 260/525 |
| 4,081,464 A | 3/1978 | Marsh et al. | 260/524 |
| 4,131,742 A | 12/1978 | Hudson | 560/241 |
| 4,141,909 A | 2/1979 | Wiedemann et al. | 260/346.4 |
| 4,145,560 A | 3/1979 | Alagy et al. | 562/412 |
| 4,150,151 A | 4/1979 | Pader et al. | 424/56 |
| 4,165,324 A | 8/1979 | Schroeder et al. | 26/346.7 |
| 4,172,209 A | 10/1979 | Vora | 562/414 |
| 4,211,881 A | 7/1980 | Horsfield et al. | 562/416 |
| 4,211,882 A | 7/1980 | Komatsu et al. | 562/416 |
| 4,215,051 A | 7/1980 | Schroeder et al. | 260/346.7 |
| 4,215,052 A | 7/1980 | Schroeder et al. | 260/346.7 |
| 4,215,053 A | 7/1980 | Palmer et al. | 260/346.7 |
| 4,215,054 A | 7/1980 | Schroeder et al. | 260/346.7 |
| 4,215,055 A | 7/1980 | Palmer et al. | 260/346.7 |
| 4,215,056 A | 7/1980 | Schroeder et al. | 260/346.7 |
| 4,217,438 A | 8/1980 | Brunelle et al. | 528/202 |
| 4,233,227 A | 11/1980 | Schroeder et al. | 260/346.7 |
| 4,234,494 A | 11/1980 | Schroeder et al. | 260/346.7 |
| 4,241,220 A | 12/1980 | Itaya et al. | 562/414 |
| 4,243,636 A | 1/1981 | Shiraki et al. | 422/225 |
| 4,250,330 A | 2/1981 | Costantini et al. | 562/409 |
| 4,278,810 A | 7/1981 | Hanotier | 562/412 |
| 4,284,523 A | 8/1981 | Darin et al. | 252/420 |
| 4,297,283 A | 10/1981 | Verbicky | 260/346.3 |
| 4,299,977 A | 11/1981 | Kuhlmann et al. | 562/416 |
| 4,314,073 A | 2/1982 | Crooks | 562/416 |
| 4,322,549 A | 3/1982 | Kuhlmann et al. | 562/416 |

(List continued on next page.)

FOREIGN PATENT DOCUMENTS

| | | |
|---|---|---|
| DE | 1.643.827 | 11/1967 |
| DE | 2.236.875 | 7/1972 |
| DE | 2.257.643 | 11/1972 |

(List continued on next page.)

OTHER PUBLICATIONS

JP2001019658, Jan. 23, 2001, Masayasu, et al., Abstract Only (1 page).
JP2002226427, Aug. 8, 2002, Takeshi, et al., Abstract Only ( 1 page).
JP2002105018, Apr. 10, 2002, Masami, et al., Abstract Only (1 page).
JP2002228050, Aug. 14, 2002, Fumio, et al., Abstract Only (2 pages).

(List continued on next page.)

Primary Examiner—Mukund J. Shah
Assistant Examiner—Zachary C. Tucker

(57) ABSTRACT

A method for the manufacture of chlorophthalic acid by liquid phase oxidation of chloro-ortho-xylene is disclosed. The chlorophthalic acid may be dehydrated to form chlorophthalic anhydride which is useful in the synthesis of polyetherimide.

51 Claims, No Drawings

U.S. PATENT DOCUMENTS

| | | | |
|---|---|---|---|
| 4,329,493 A | 5/1982 | Hashizume et al. | 562/414 |
| 4,334,086 A | 6/1982 | Hanotier et al. | 562/413 |
| 4,339,599 A | 7/1982 | Jongsma | 562/412 |
| 4,370,487 A | 1/1983 | Meyer et al. | 549/242 |
| 4,387,243 A | 6/1983 | Naim et al. | 562/413 |
| 4,389,334 A | 6/1983 | Weinert, Jr. et al. | 252/429 |
| 4,436,922 A | 3/1984 | Kita et al. | 549/251 |
| 4,447,646 A | 5/1984 | Johnson et al. | 562/487 |
| 4,459,365 A | 7/1984 | Suzuki et al. | 502/24 |
| 4,469,878 A | 9/1984 | Kaneyasu et al. | 549/248 |
| 4,477,380 A | 10/1984 | Knips et al. | 260/385 |
| 4,481,304 A | 11/1984 | Sato et al. | 502/209 |
| 4,489,204 A | 12/1984 | Neri et al. | 549/248 |
| 4,582,912 A | 4/1986 | Saleh et al. | 549/239 |
| 4,587,350 A | 5/1986 | Kilner et al. | 549/245 |
| 4,593,122 A | 6/1986 | Hashizume et al. | 562/414 |
| 4,594,449 A | 6/1986 | Takuma et al. | 562/416 |
| 4,603,220 A | 7/1986 | Feld | 562/416 |
| 4,605,757 A | 8/1986 | Feld | 562/416 |
| 4,632,998 A | 12/1986 | Geissen et al. | 549/248 |
| 4,675,420 A | 6/1987 | Block et al. | 549/248 |
| 4,677,240 A | 6/1987 | Carlson et al. | 585/488 |
| 4,719,311 A | 1/1988 | Partenheimer | 562/413 |
| 4,725,570 A | 2/1988 | Sikkenga et al. | 502/204 |
| 4,755,622 A | 7/1988 | Schammel et al. | 562/413 |
| 4,769,487 A | 9/1988 | Hundley et al. | 562/413 |
| 4,769,489 A | 9/1988 | Abrams et al. | 562/416 |
| 4,777,287 A | 10/1988 | Zeitlin et al. | 562/414 |
| 4,785,121 A | 11/1988 | Leone-Bay et al. | 549/246 |
| 4,786,753 A | 11/1988 | Partenheimer et al. | 562/416 |
| 4,792,621 A | 12/1988 | Abrams | 562/414 |
| 4,816,601 A | 3/1989 | Lowry et al. | 562/413 |
| 4,827,025 A | 5/1989 | Shiraki et al. | 562/414 |
| 4,830,789 A | 5/1989 | Hinenoya et al. | 660/546 |
| 4,845,241 A | 7/1989 | Edwards et al. | 549/260 |
| 4,845,274 A | 7/1989 | Schammel et al. | 562/413 |
| 4,855,491 A | 8/1989 | Chew et al. | 562/414 |
| 4,855,492 A | 8/1989 | Hundley | 562/414 |
| 4,876,386 A | 10/1989 | Holzhauer et al. | 562/414 |
| 4,877,900 A | 10/1989 | Tamaru et al. | 562/413 |
| 4,879,387 A | 11/1989 | Hara | 549/248 |
| 4,895,978 A | 1/1990 | Darin et al. | 562/416 |
| 4,900,480 A | 2/1990 | Litz et al. | 261/36.1 |
| 4,900,865 A | 2/1990 | Hussmann et al. | 562/412 |
| 4,906,771 A | 3/1990 | Young et al. | 562/416 |
| 4,908,471 A | 3/1990 | Leuck et al. | 560/77 |
| 4,910,175 A | 3/1990 | Michel et al. | 502/24 |
| 4,939,297 A | 7/1990 | Browder et al. | 562/485 |
| 4,950,786 A | 8/1990 | Sanchez et al. | 562/416 |
| 4,952,721 A | 8/1990 | Fjare | 560/131 |
| 4,978,760 A | 12/1990 | Spohn | 549/246 |
| 4,992,579 A | 2/1991 | Schammel | 562/413 |
| 4,992,580 A | 2/1991 | Partenheimer | 562/416 |
| 4,996,353 A | 2/1991 | Lee et al. | 562/412 |
| 5,003,088 A | 3/1991 | Spohn et al. | 549/246 |
| 5,004,830 A | 4/1991 | Park et al. | 562/413 |
| 5,028,737 A | 7/1991 | Sanchez | 562/416 |
| 5,041,633 A | 8/1991 | Partenheimer et al. | 562/413 |
| 5,049,682 A | 9/1991 | Tang et al. | 549/246 |
| 5,055,612 A | 10/1991 | Tachibana et al. | 562/416 |
| 5,059,697 A | 10/1991 | Fertel et al. | 549/246 |
| 5,081,290 A | 1/1992 | Partenheimer et al. | 562/416 |
| 5,082,959 A | 1/1992 | Ernst et al. | 556/438 |
| 5,087,741 A | 2/1992 | Tennant et al. | 562/414 |
| 5,095,141 A | 3/1992 | Schammel et al. | 562/414 |
| 5,095,142 A | 3/1992 | Janulis | 562/414 |
| 5,095,143 A | 3/1992 | Heberer et al. | 562/416 |
| 5,095,146 A | 3/1992 | Zeitlin et al. | 562/486 |
| 5,099,064 A | 3/1992 | Huber, Jr. et al. | 562/414 |
| 5,112,992 A | 5/1992 | Belmonte et al. | 549/245 |
| 5,132,450 A | 7/1992 | Tanaka et al. | 562/414 |
| 5,169,820 A | 12/1992 | Ueda et al. | 502/209 |
| 5,183,933 A | 2/1993 | Harper et al. | 562/414 |
| 5,185,451 A | 2/1993 | Stults et al. | 548/418 |
| 5,206,391 A | 4/1993 | Seper et al. | 549/246 |
| 5,210,223 A | 5/1993 | Chen et al. | 549/247 |
| 5,225,573 A | 7/1993 | Shorr et al. | 549/246 |
| 5,225,574 A | 7/1993 | Aichinger et al. | 549/248 |
| 5,225,575 A | 7/1993 | Ivanov et al. | 549/249 |
| 5,229,482 A | 7/1993 | Brunelle | 528/125 |
| 5,229,527 A | 7/1993 | Ueda et al. | 549/248 |
| 5,233,054 A | 8/1993 | Tang et al. | 549/246 |
| 5,235,071 A | 8/1993 | Ueda et al. | 549/248 |
| 5,242,643 A | 9/1993 | Kim et al. | 422/129 |
| 5,250,724 A | 10/1993 | Fumagalli et al. | 562/416 |
| 5,264,588 A | 11/1993 | Krishnan | 548/476 |
| 5,300,201 A | 4/1994 | Seper et al. | 204/157.6 |
| 5,322,954 A | 6/1994 | Seper et al. | 549/246 |
| 5,324,702 A | 6/1994 | Yoo et al. | 502/204 |
| 5,332,707 A | 7/1994 | Karayannis et al. | 502/113 |
| 5,334,754 A | 8/1994 | Sumner, Jr. et al. | 562/416 |
| 5,342,968 A | 8/1994 | Brugge et al. | 549/241 |
| 5,359,133 A | 10/1994 | Nazimok et al. | 562/413 |
| 5,371,283 A | 12/1994 | Kingsley et al. | 562/416 |
| 5,449,820 A | 9/1995 | Fukui et al. | 562/486 |
| 5,453,538 A | 9/1995 | Broeker et al. | 562/409 |
| 5,473,101 A | 12/1995 | Johnstone et al. | 562/416 |
| 5,510,521 A | 4/1996 | McGehee et al. | 562/414 |
| 5,557,009 A | 9/1996 | Izumisawa et al. | 562/412 |
| 5,574,172 A | 11/1996 | Katsuro et al. | 549/246 |
| 5,596,129 A | 1/1997 | Murashige et al. | 562/414 |
| 5,612,007 A | 3/1997 | Abrams | 422/189 |
| 5,637,764 A | 6/1997 | Rohrscheid et al. | 562/416 |
| 5,679,847 A | 10/1997 | Ohkoshi et al. | 562/416 |
| 5,683,553 A | 11/1997 | Baur et al. | 203/1 |
| 5,693,856 A | 12/1997 | Ramachandran et al. | 562/414 |
| 5,696,285 A | 12/1997 | Roby | 562/416 |
| 5,705,682 A | 1/1998 | Ohkoshi et al. | 562/414 |
| 5,723,656 A | 3/1998 | Abrams | 562/412 |
| 5,739,384 A | 4/1998 | Albillos et al. | 562/414 |
| 5,763,648 A | 6/1998 | Hashizume et al. | 562/414 |
| 5,763,649 A | 6/1998 | Fukuhara | 562/416 |
| 5,770,764 A | 6/1998 | Zeitlin et al. | 562/412 |
| 5,830,974 A | 11/1998 | Schmidhauser et al. | 528/125 |
| 5,880,313 A | 3/1999 | Zaima et al. | 562/414 |
| 5,919,977 A | 7/1999 | Murakami et al. | 562/412 |
| 5,925,786 A | 7/1999 | Isayama et al. | 562/412 |
| 5,958,821 A | 9/1999 | Ishii et al. | 502/167 |
| 5,959,140 A | 9/1999 | Okoshi et al. | 562/414 |
| 5,961,942 A | 10/1999 | Turner et al. | 423/240 |
| 5,969,164 A | 10/1999 | Budge et al. | 549/508 |
| 5,981,420 A | 11/1999 | Nakano et al. | 502/155 |
| 6,018,077 A | 1/2000 | Ohkoshi et al. | 562/414 |
| 6,020,522 A | 2/2000 | Ishii et al. | 562/410 |
| 6,034,269 A | 3/2000 | Turner et al. | 562/412 |
| 6,114,574 A | 9/2000 | Sen et al. | 562/410 |
| 6,114,575 A | 9/2000 | McMahon et al. | 562/414 |
| 6,133,476 A | 10/2000 | Lin | 562/486 |
| 6,150,553 A | 11/2000 | Parten | 560/248 |
| 6,153,790 A | 11/2000 | June et al. | 562/414 |
| 6,160,170 A | 12/2000 | Codignola | 562/413 |
| 6,175,038 B1 | 1/2001 | Jhung et al. | 562/412 |
| 6,180,822 B1 | 1/2001 | Jhung et al. | 562/412 |
| 6,194,607 B1 | 2/2001 | Jhung et al. | 562/412 |
| 6,232,495 B1 | 5/2001 | Vassiliou et al. | 562/543 |
| 6,242,643 B1 | 6/2001 | Matsuoka et al. | 562/416 |
| 6,255,525 B1 | 7/2001 | Sikkenga et al. | 562/412 |
| 6,268,528 B1 | 7/2001 | Machida et al. | 562/412 |
| 6,307,099 B1 | 10/2001 | Turner et al. | 562/412 |
| 6,355,834 B1 | 3/2002 | Brownscombe et al. | 562/412 |
| 6,355,835 B1 | 3/2002 | Kulsrestha et al. | 562/417 |

| | | | |
|---|---|---|---|
| 6,362,367 B2 | 3/2002 | Braithwaite et al. | 562/531 |
| 6,380,399 B1 | 4/2002 | Okuno et al. | 549/250 |
| 6,410,753 B2 | 6/2002 | Tanaka et al. | 549/245 |
| 6,458,994 B2 | 10/2002 | Okoshi et al. | 562/416 |
| 6,465,685 B1 * | 10/2002 | Phelps et al. | 562/422 |
| 6,476,257 B1 | 11/2002 | Park et al. | 562/412 |
| 6,507,913 B1 | 1/2003 | Shamir | 713/200 |
| 2001/0016667 A1 | 8/2001 | Matsuoka et al. | 562/416 |
| 2001/0034459 A1 | 10/2001 | Meudt et al. | 562/409 |
| 2001/0041811 A1 | 11/2001 | Sikkenga et al. | 562/416 |
| 2002/0002303 A1 | 1/2002 | Rosen | 562/414 |
| 2002/0010346 A1 | 1/2002 | Tanaka et al. | 549/239 |
| 2002/0016501 A1 | 2/2002 | Okoshi et al. | 562/416 |
| 2002/0091285 A1 | 7/2002 | Housley et al. | 562/412 |
| 2002/0099240 A1 | 7/2002 | Ohkoshi et al. | 562/414 |

FOREIGN PATENT DOCUMENTS

| | | |
|---|---|---|
| EP | 0 021 747 | 6/1980 |
| EP | 0 026 507 | 8/1980 |
| EP | 0 066 436 | 5/1982 |
| EP | 0 087 678 | 2/1983 |
| EP | 0 099 078 | 7/1983 |
| EP | 0 135 341 | 8/1984 |
| EP | 0 137 548 | 9/1984 |
| EP | 0 077 334 | 11/1984 |
| EP | 0 256 352 | 7/1987 |
| EP | 0 257 788 B1 | 7/1987 |
| EP | 0 257 788 A1 | 7/1987 |
| EP | 0 261 892 | 9/1987 |
| EP | 0 279 288 | 2/1988 |
| EP | 0 318 205 | 11/1988 |
| EP | 0 375 812 | 12/1988 |
| EP | 0 330 219 | 2/1989 |
| EP | 0 334 049 | 2/1989 |
| EP | 0 338 215 | 2/1989 |
| EP | 0 341 813 | 3/1989 |
| EP | 0 343 991 | 5/1989 |
| EP | 0 361 798 | 9/1989 |
| EP | 0 417 691 | 9/1990 |
| EP | 0 440 593 | 1/1991 |
| EP | 0 639 174 | 11/1991 |
| EP | 0 593 546 | 6/1992 |
| EP | 0 641 303 | 5/1993 |
| EP | 0 601 177 | 6/1993 |
| EP | 0 673 910 | 3/1995 |
| EP | 0 682 000 | 5/1995 |
| EP | 0 682 005 | 5/1995 |
| EP | 0 734 372 | 9/1995 |
| EP | 0 713 856 | 11/1995 |
| EP | 0 719 754 | 12/1995 |
| EP | 0 764 626 | 9/1996 |
| EP | 0 781 754 | 12/1996 |
| EP | 0 796 837 | 3/1997 |
| EP | 0 818 433 | 7/1997 |
| EP | 0 889 021 | 10/1997 |
| EP | 0 860 423 | 2/1998 |
| EP | 0 962 442 | 6/1999 |
| EP | 1 162 200 A2 | 12/2001 |
| EP | 1 225 164 A1 | 7/2002 |
| FR | 832995 | 11/1956 |
| FR | 856245 | 12/1957 |
| FR | 970491 | 9/1964 |
| FR | 970492 | 9/1964 |
| FR | 1574651 | 9/1980 |
| GB | 856245 | 12/1960 |
| GB | 2 072 162 | 3/1980 |
| JP | 55111442 | 2/1979 |
| JP | 01319457 | 8/1988 |
| JP | A K05 339204 C1.1 | 12/1993 |
| WO | WO 95/09143 | 4/1995 |
| WO | WO 96/30327 | 10/1996 |
| WO | WO 96/31455 | 10/1996 |
| WO | WO 96/40610 | 12/1996 |
| WO | WO 97/27168 | 7/1997 |
| WO | WO 97/36673 | 10/1997 |
| WO | WO 99/05086 | 2/1999 |
| WO | WO 99/14178 | 3/1999 |
| WO | WO 99/14179 | 3/1999 |
| WO | WO 99/31038 | 6/1999 |
| WO | WO 99/37599 | 7/1999 |
| WO | WO 99/42430 | 8/1999 |
| WO | WO 99/54274 | 10/1999 |
| WO | WO 99/59953 | 11/1999 |
| WO | WO 00/37406 | 6/2000 |
| WO | WO 00/37407 | 6/2000 |
| WO | WO 00/66529 | 9/2000 |
| WO | WO 00/63146 | 10/2000 |
| WO | WO 00/66529 | 11/2000 |
| WO | WO 01/14308 | 3/2001 |
| WO | WO 01/21571 | 3/2001 |
| WO | WO 01/92195 | 12/2001 |
| WO | WO 02/30861 | 4/2002 |

OTHER PUBLICATIONS

JP2002113346, Apr. 16, 2002, Jae–Sung, Abstract Only (2 pages).

JP2001288139, Oct. 16, 2001, Naoki, et al., Abstract Only (1 page).

JP2001002620, Jan. 9, 2001, Kazuyuki, et al., Abstract Only (1 page).

Ullmann's Encyclopedia of Industrial Chemistry, vol. A3, pp. 555–569, 1985.

Jhung, et al., "Effects of Alkali Metals on the Liquid Phase Oxidation of P–Xylene", Applied Catalysis A: General 230 (2002) 31–40.

U.S. patent application No. 10/174,096, Method for Removing Impurities from Oxidation Products, Filed Jun. 18, 2002.

Elvers, et al., Ullmann's Encyclopedia of Industrial Chemistry, Fifth, Completely Revised Edition, vol. A20, pp. 181–211, 1992.

Shcherbina, et al., Kinetics and Catalysis, vol. 19, No. 4, Part 2 (Jul.–Aug. 1978)(Russian)(4 pages).

"Study of the Effect of a Substituent on the Process of Liquid Phase Catalytic Oxidation of 4–Substituted o–Xylenes", Riga Polytechnic Institute (Sep. 4, 1972) (7 pages).

Nazarenko, et al. "Production of Monochlorophthalic acids by liquid phase catalytic oxidation of chloro–o–xylenes" Ukrainskiy Khimicheskiy Zhurnal. vol. 50, No. 6. 1984. pp. 644–647.

Greene, et al. "The Journal of Organic Chemistry" vol. 38. No. 6. pp. 1242–1245 Mar. 23, 1973.

Chervinakil, et al. "Kinetics of the Oxidation of Chloro and Nitro–o–Xylenes with Molecular Oxygen". Russian Journal of Physical Chemistry vol. 43. No. 8. pp. 1154–1157 (1969).

Bhatia, et al. "Cobalt (II)–Catalyzed Reaction of Aldehydes with Acetic Anhydride Under an Oxygen Atmosphere: Scope and Mechanism". J. Org. Chem. 1993. vol. 58. No. 20. pp. 5518–5523 (Abstract).

Hay, et al. "Autoxidation Reactions Catalyzed by Cobalt Acetate Bromide" Canadian Journal of Chemistry. vol. 43. pp. 1306–1317. (1965).

Li, et al. "Oxidation of alkynes by cobalt acetate bromide: a new mode of action for an improtant industrial catalyst". Journal of Molecular Catalysis A: Chemical 145 (1999) pp. 111–120.

Maki, et al. "Antidiabetic Drugs to Benzoquinone and Naphthoquinone Dyes" Ullmann's Encyclopedia of Industrial Chemistry. vol. A3. pp. 555–569. (1985).

Kamiya. "The Autoxidation of Tetralin Catalysed by Cobalt Salt and Sodium Bromide in Acetic Acid" vol. 22. pp. 2029–2038. (1966).

Towae, et al. "Photography to Plastics, Processing" Ullmann's Encyclopedia of Industrial Chemistry. vol. A20. pp. 181–211. (1992).

W. Partenheimer. "Methodology and scope of metal/bromide autoxidation of hydrocarbons" Catalysis Today 23 pp. 69–158. (1995).

Landau, et al. "Development of the M–C Process". SCOPE. vol. 64. No. 10. pp. 20–26. (Oct. 1968).

Partenheimer. "Characterization of the reaction of cobalt (II) acetate, dioxygen and acetic acid, and its significance in autoxidation reactions". Journal of Molecular Catalysis pp. 35–46. (1991).

Iwahama, et al. "Production of Hydrogen Peroxide via Aerobic Oxidation of Alcohols Catalyzed by N–Hydroxyphthalimide" Organic–Process Research & Development. vol. 4. No. 2. pp. 94–97. (2000).

Suresh, et al. "Engineering Aspects of Industrial Liquid–Phase Air Oxidation of Hydrocarbons". Ind. Eng. Chem. Res. vol. 39 pp. 3958–3997. (2000).

Akai, et al. "X–Ray Absorption Fine Structure (XAFS) Studies on Cobalt (II) Bromo Complexes in Acetic Acid Solutions" Bull. Chem. Soc. Jpn. vol. 72. pp. 1239–1246. (1999).

Shiraishi, et al. "Selective synthesis of 2, 6–naphthalenedicarboxylic acid by use of cyclodextrin as catalyst" Journal of Molecular Catalysis A. Chemical 139. pp. 149–158 (Abstract) (1999).

Szymanska–Buzar, et al. "Activation of Hydrocarbon Molecules via Co(III)–RH Interaction in Trifluoroacetic Acid Solution" Journal of Molecular Catalysis. vol. 5 pp. 341–348. (1979).

Metelski, et al. "Mechanistic Role of Benzylic Bromides in the Catalytic Autoxidation of Methylarenes" Articles. vol. 29 pp. 2434–2439. (2000).

Jiao, et al. "Kinetics of Manganese (III) Acetate in Acetic Acid: Generation of Mn(III) with Co(III), Ce(IV), and Dibromide Radicals; Reactions of Mn(III) with Mn(II), Co(II), Hydrogen Bromide, and Alkali Bromides". Inorg. Chem.vol. 29. pp. 1549–1554 (2000).

Partenheimer, et al. "Nature of the Co–Mn–Br Catalyst in the Methylaromatic Compounds Process". Catalytic Selective Oxidation. Chapter 7. pp. 81–88. (1992).

Chester, et al. "Zirconium Cocatalysis of the Cobalt–Catalyzed Autoxidation of Alkylaromatic Hydrocarbons" Journal of Catalysis vol. 46. pp. 308–319 (1977).

Rogovin, et al. "Silicate xerogels containing cobalt as heterogeneous catalysts for the side–chain oxidation of alkyl aromatic compounds with tert–butyl hydroperoxide" Journal of Molecular Catalysis A: Chemical vol. 138. pp. 315–318. (1999).

Chavan, et al. "Formation and role of cobalt and maganese cluster complexes in the oxidation of p–xylene". Journal of Molecular Catalysis A: Chemical 161. pp. 49–64. (2000).

Graham H. Jones "A Mechanistic Study of the Origins of Synergy and Antagonism in the Cobalt Acetate Bromide and Manganese Acetate Bromide Catalysed Autoxidation of p–Xylene". Imperial Chemical Industries Ltd., Paper E/15/82. Received Jan. 26, 1982. pp. 2137–2163.

Graham H. Jones "A Kinetic and Mechanistic Study of the Redox Chemistry of Cobalt Acetate in Aqueous Acetic Acid". Imperial Chemical Industries Ltd .Paper E/032/81 Received Feb. 20, 1981. pp. 2801–2868.

Bryant, et al. "Mobil's Process for TPA" Chemical Engineering Progress. vol. 67. No. 9. pp. 69–75. (1971).

Graham H. Jones "p–Xylene Autoxidation Studies. Oxidation of Cobalt (II) and Manganese (II) Acetates by Peracids". J.C.S. Chem. Com. pp. 536–537. (1979).

Kamiya, et al. "The Autoxidation of Aromatic Hydrocarbons Catalyed with Cobaltic Acetate in Acetic Acid Solution" Journal of Catalysis vol. 25. pp. 326–333 (1972).

Scott, et al. "Kinetics of the Cobalt–Catalyzed Autoxidation of Toluene in Acetic Acid" The Journal of Physical Chemistry. vol. 76. No. 11 pp. 1520–1524. (1972).

R.A. Sheldon." Liquid Phase Autoxidation" Catalytic Oxidation pp. 150–175. (1995).

Clark, et al. "Catalytic oxidation of the side chain of alkylaromatics using a triphasic system" Synthetic Communications. vol. 30 No. 20. pp. 2731–2735 (2000).

Serija, et al. "Study of the Effect of a Substituent on the Process of Liquid Phase Catalytic Oxidation of 4–Substituted o–Xylenes" Riga Polytechnic Institute. Received Sep. 4, 1972. pp. 72–74.

Park, et al. Phthalic Acids and Other Benzeneolycar–Boxylic Acids' vol. 18. pp. 991–1043.

Kataliz, et al. "Kinetics and Catalysis" Russian Original. vol. 19. No. 4. Part 2. Jul.–Aug. 1978.

Bhatia, et al. "Cobalt (II)–Catalyzed Reaction of Aldehydes with Acetic Anhydride Under an Oxygen Atmosphere: Scope and Mechanism" J. Org. Chem. vol. 58. No. 20. pp. 5518–5523 (1993) (Abstract).

Kulakov, et al. "Study of the mechanism of the oxidation of aromatic hydrocarbons and development of technology of synthesis of terephthalic acid" Mendeleevsk, S'ezd Obshch. Prikl. Khim. 11th vol. 2 pp. 323–324 (Abstract) (1975).

Partenheimer. "Novel catalytic characteristics of the Co/Mn/Cl/Br liquid phase oxidation catalyst (1)" Chem. Ind. pp. 357–368 (Abstract) (1998).

Partenheimer. "Thermodynamic and kinetic studies to elucidate the Amoco Co/Mn/Br. autooxidation ("MC") catalyst" Act. Dioxygen Homogeneous Catal. Oxid., 5th pp. 474 (1993) (Abstract).

Gipe, et al. "Catalysts by rational design: prediction and confirmation of the properties of the Co/Ce/Br liquid–phase autoxidation catalyst based on the kinetic similarity to the Co/Mn/Br catalyst" Stud. Surf. Sci. Catal. pp. 1117–1127. (1997) (Abstract).

Uzulniece et al., "Liquid–phase catalytic oxidation of 4–bromo–o–xylene". Chemical Abstracts + Indexes, American Chemical Society. vol. 90. No. 5 (1979) XP002165078 (Abstract Only).

International Search Report Mailed on Jul. 15, 2003.

* cited by examiner

US 6,657,067 B2

METHOD FOR THE MANUFACTURE OF CHLOROPHTHALIC ANHYDRIDE

BACKGROUND OF INVENTION

This invention relates to liquid phase oxidation of halogen substituted alkyl aromatic compounds. In particular, the invention relates to liquid phase oxidation of chloro-ortho-xylene to produce chlorophthalic acid which can be dehydrated to produce chlorophthalic anhydride.

Liquid phase oxidation has long been used to produce dicarboxylic acids from dialkyl benzenes. Of particular interest has been the oxidation of dimethyl benzene (xylene) to phthalic acid, especially the oxidation of para-xylene to terephthalic acid, which is used in the production of polybutylene terephthalate. The liquid phase oxidation of xylene to phthalic acid requires the use of a catalyst, typically a cobalt/manganese/bromide catalyst system, and is generally performed in a carboxylic acid solvent such as acetic acid. The catalyst system may be augmented by the use of a co-catalyst such as zirconium, hafnium or cerium. Phthalic acid is an easily isolable solid, which can be filtered out of the reaction mixture.

Liquid phase oxidation, using a cobalt/manganese/bromide catalyst system and a carboxylic acid solvent, has also been applied to halogenated xylene with some success. The oxidation of the halogenated xylene is more difficult than the oxidation of xylene due to presence of a halogen, which is an electron withdrawing substituent, on the benzene ring. The greater difficulty in oxidation results in a lower reaction selectivity and a larger amount of partial oxidation and side products than seen in the liquid phase oxidation of xylene under similar conditions. Additionally, halogenated phthalic acid is difficult to separate from the partial oxidation and side products, even by distillation. Thus it is clear that in order for a method of halogenated xylene liquid phase oxidation to be commercially successful the reaction yield and the reaction selectivity must be very high. Optimally, for a useful commercial process, the reaction selectivity should be high enough to result in only negligible amounts of partial oxidation and side products thus removing the need for isolation of halophthalic acid.

SUMMARY OF INVENTION

A method for the manufacture of chlorophthalic acid comprises forming a reaction mixture comprising a mixture of about 5 to about 3 parts by weight of acetic acid to 1 part by weight of chloro-ortho-xylene, about 0.25 to about 2 mole percent, based on the chloro-ortho-xylene, of a cobalt source, about 0.1 to about 1 mole percent, based on the chloro-ortho-xylene, of a manganese source, about 0.01 to about 0.1 mole percent, based on the chloro-ortho-xylene, of a source of a metal selected from zirconium, hafnium and mixtures thereof, and about 0.02 to about 0.05 mole percent, based on the chloro-ortho-xylene, of a bromide source; maintaining the reaction mixture at a pressure of at least about 1600 kilopascals (KPa) and at a temperature of about 150° C. to about 170° C.; introducing a molecular oxygen containing gas to the reaction mixture at a rate of at least about 1.0 normal $m^3$ of gas/hour per kilogram (kg) of chloro-ortho-xylene in the reaction mixture to create an oxygen containing off gas from the reaction mixture, wherein the off gas oxygen concentration is less than about one percent by volume of the off gas; maintaining the introduction of the molecular oxygen containing gas until the off gas oxygen concentration exceeds about 3 percent by volume of the off gas; modifying the introduction of the molecular oxygen containing gas to maintain the off gas oxygen concentration below about 5 percent by volume of the off gas; and maintaining the modified introduction of the molecular oxygen containing gas for a time sufficient to provide at least about 90 percent conversion of the chloro-ortho-xylene to chlorophthalic acid.

In another aspect, the method for the manufacture of chlorophthalic acid comprises forming a reaction mixture comprising a mixture of about 5 to about 3 parts by weight of acetic acid to 1 part by weight of chloro-ortho-xylene, about 0.8 to about 1.2 mole percent, based on the chloro-ortho-xylene, of a cobalt source, about 0.4 to about 0.6 mole percent, based on the chloro-ortho-xylene, of a manganese source, about 0.04 to about 0.06 mole percent, based on the chloro-ortho-xylene, of a source of an ionic metal selected from zirconium, hafnium and mixtures thereof, and less than about 0.04 mole percent, based on the chloro-ortho-xylene, of a bromide source; maintaining the reaction mixture at a pressure of at least about 1600 KPa and at a temperature of about 150° C. to about 170° C.; introducing air to the reaction mixture at a rate of at least about 1.0 normal $m^3$ of oxygen/kg of chloro-ortho-xylene in the reaction mixture to create an oxygen containing off gas, wherein the off gas oxygen concentration is less than about one percent by volume of the off gas; maintaining the introduction of the air until the off gas oxygen-concentration exceeds about 3 percent by volume of the off gas; modifying the introduction of air so as to maintain the off gas oxygen concentration below about 5 percent by volume of the off gas; and maintaining the modified introduction of air for a time sufficient to provide at least about 90 percent conversion of the chloro-ortho-xylene to chlorophthalic acid.

In another embodiment, a method for the manufacture of chlorophthalic anhydride comprises forming a reaction mixture comprising a mixture of about 5 to about 3 parts by weight of acetic acid to 1 part by weight of a chloro-ortho-xylene, about 0.25 to about 2 mole percent, based on the chloro-ortho-xylene, of a cobalt source, about 0.1 to about 1 mole percent, based on the chloro-ortho-xylene, of a manganese source, about 0.01 to about 0.1 mole percent, based on the chloro-ortho-xylene, of a source of a metal selected from zirconium, hafnium and mixtures thereof, and about 0.02 to about 0.05 mole percent, based on the chloro-ortho-xylene, of a bromide source; maintaining the reaction mixture at a pressure of at least about 1600 KPa and at a temperature of about 150° C. to about 170° C.; introducing a molecular oxygen containing gas to the reaction mixture at a rate of at least about 1.0 normal $m^3$ of oxygen/kg of chloro-ortho-xylene in the reaction mixture to create an oxygen containing off gas, wherein the off gas oxygen concentration is less than about one percent by volume of the off gas; maintaining the introduction of the molecular oxygen containing gas until the off gas oxygen concentration exceeds about 3 percent by volume of the off gas; modifying the introduction of the molecular oxygen containing gas to maintain the off gas oxygen concentration below about 5 percent by volume of the off gas; maintaining the modified introduction of the molecular oxygen containing gas for a time sufficient to provide at least about 90 percent conversion of the chloro-ortho-xylene to chlorophthalic acid; removing the acetic acid and any water formed as a result of the reaction, by distillation; and dehydrating the chlorophthalic acid to form chlorophthalic anhydride.

In another aspect, the method for the manufacture of chlorophthalic anhydride comprises forming a reaction mixture comprising a mixture of about 5 to about 3 parts by weight of acetic acid to 1 part by weight of a chloro-ortho-xylene, about 0.8 to about 1.2 mole percent, based on the chloro-ortho-xylene, of cobalt acetate or cobalt acetate hydrate, about 0.4 to about 0.6 mole percent, based on the chloro-ortho-xylene, of manganese acetate or manganese acetate hydrate, about 0.04 to about 0.06 mole percent, based on the chloro-ortho-xylene, of zirconium acetate or zirconium acetate hydrate, and less than about 0.04 mole percent, based on the chloro-ortho-xylene, of sodium bromide or hydrogen bromide; maintaining the reaction mixture-at a pressure of at least about 1600 KPa and at a temperature of about 150° C. to about 170° C.; introducing air to the reaction mixture at a rate of at least about 1.0 normal m³ of oxygen/kg of chloro-ortho-xylene in the reaction mixture to create an oxygen containing off gas, wherein the off gas oxygen concentration is less than about one percent by volume of the off gas, maintaining the introduction of air until the off gas oxygen concentration exceeds about 3 percent by volume of the off gas; modifying the introduction of air to maintain the off gas oxygen concentration below about 5 percent by volume of the off gas and maintaining the modified introduction of air for a time sufficient to provide at least about 90 percent conversion of the chloro-ortho-xylene to chlorophthalic acid; removing the acetic acid and any water formed as a result of the reaction by distillation; recycling the acetic acid; and dehydrating the chlorophthalic acid to form chlorophthalic anhydride.

In another embodiment, a method for the manufacture of polyetherimide comprises forming a reaction mixture comprising a mixture of about 5 to about 3 parts by weight of acetic acid to 1 part by weight of a chloro-ortho-xylene, about 0.25 to about 2 mole percent, based on the chloro-ortho-xylene, of a cobalt source, about 0.1 to about 1 mole percent, based on the chloro-ortho-xylene, of a manganese source, about 0.01 to about 0.1 mole percent, based on the chloro-ortho-xylene, of a source of metal selected from zirconium, hafnium and mixtures thereof, about 0.02 to about 0.05 mole percent, based on the chloro-ortho-xylene, of a bromide source; maintaining the reaction mixture at a pressure of at least about 1600 KPa and a temperature of about 150° C. to about 170° C.; introducing a molecular oxygen containing gas to the reaction mixture at a rate of at least about 1.0 normal m³ of oxygen/kg of chloro-ortho-xylene in the reaction mixture to create an oxygen containing off gas, wherein the off gas oxygen concentration is less than about one percent by volume of the off gas; maintaining the introduction of the molecular oxygen containing gas until the off gas oxygen concentration exceeds about 3 percent by volume of the off gas; modifying the introduction of the molecular oxygen containing gas to maintain the off gas oxygen concentration below about 5 percent by volume of the off gas and maintaining the modified introduction of the molecular oxygen containing gas for a time sufficient to provide at least about 90 percent conversion of the chloro-ortho-xylene to chlorophthalic acid with less than about 200 parts per million (ppm) of chlorophthalide removing the acetic acid and any water formed as a result of the reaction by distillation; dehydrating the chlorophthalic acid i to form chlorophthalic anhydride; reacting the chlorophthalic anhydride with 1,3-diaminobenzene to form bis(chlorophthalimide) (II)

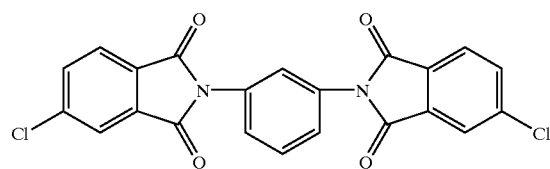

; and reacting bis(chlorophthalimide) (II) with an alkali metal salt of a dihydroxy substituted aromatic hydrocarbon having the formula (IV)

wherein $A^2$ is a divalent aromatic hydrocarbon radical to form the polyetherimide.

DETAILED DESCRIPTION

A method for the manufacture of chlorophthalic acid comprises forming a reaction mixture comprising a mixture of about 5 to about 3 parts by weight of acetic acid to 1 part by weight of a chloro-ortho-xylene, about 0.25 to about 2 mole percent, based on the chloro-ortho-xylene, of a cobalt source, about 0.1 to about 1 mole percent, based on the chloro-ortho-xylene, of a manganese source, about 0.01 to about 0.1 mole percent, based on the chloro-ortho-xylene, of a source of a metal selected from zirconium, hafnium and mixtures thereof, and about 0.02 to about 0.05 mole percent, based on the chloro-ortho-xylene, of a bromide source. The reaction mixture is maintained at a pressure of at least about 1600 KPa and at a temperature of about 150° C. to about 170° C. A molecular oxygen containing gas is introduced to the reaction mixture at a rate of at least about 1.0 normal m³ of oxygen containing gas/hour per kg of chloro-ortho-xylene in the reaction mixture to create an oxygen containing off gas, wherein the off gas oxygen concentration is less than about one percent by volume of the off gas. The introduction of the molecular oxygen containing gas is maintained until the off gas oxygen concentration exceeds about 3 percent by volume of the off gas and then the introduction of the molecular oxygen containing gas is modified so as to maintain the off gas oxygen concentration below about 5 percent by volume. The modified introduction of the molecular oxygen containing gas is maintained for a time sufficient to provide at least about 90 percent conversion of the chloro-ortho-xylene to chlorophthalic acid.

Using the method for manufacture of chlorophthalic acid and anhydride described herein, the high yield synthesis of high purity chlorophthalic acid and anhydride is possible on a large scale employing hundreds of kilograms of chloro-ortho-xylene by liquid phase oxidation in the presence of about 0.25 to about 2 mole percent (mol %) of a cobalt source, about 0.1 to about 1 mol % of a manganese source, about 0.01 to about 0.1 mol % of a source of a metal selected from zirconium; hafnium and mixtures thereof, and about 0.02 to about 0.05 mol % of a bromide source. Applicants have discovered that in large scale liquid phase oxidations employing chloro-ortho-xylene the amount of bromide can have a significant impact on the amount of impurities present in the final product. The use of decreasing molar percentages of bromide result in a product, either chlorophthalic acid or anhydride, with a decreased level of impurities such as chlorophthalide. While the reasons for this phenomenon are not clearly understood it is contemplated that even lower levels of bromide, molar percentages less than about 0.02, may be useful in producing high purity chlorophthalic acid or anhydride in even larger scale liquid phase oxidations such as those employing thousands of kilograms of chloro-ortho-xylene.

Chloro-ortho-xylene suitable for use in the oxidation has the structure (IV)

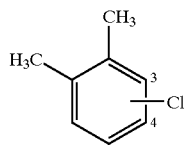

(IV)

The chlorine substituent may be in the 3 position (the 3-isomer) or in the 4 position (the 4-isomer). The chloro-ortho-xylene used in the liquid-phase oxidation may also be a mixture of the 3-isomer and the 4-isomer.

The liquid phase oxidation preferably employs acetic acid as a solvent although other lower carboxylic acids may be employed. Preferably glacial acetic acid is used but acetic acid with a water content of up to 3 percent may be employed. Typically the acetic acid is present in an amount of 5 to 3 parts by weight to 1 part by weight of chloro-ortho-xylene.

Suitable molecular oxygen containing gases include gases or combinations of gases which are a source of molecular oxygen($O_2$), for example 100 percent oxygen and mixtures of oxygen with an inert gas with a sufficient concentration of oxygen to effect oxidation. Sufficient oxygen concentrations typically are greater than or equal to about 6 percent oxygen, preferably greater than or equal to about 15 percent, more preferably greater than or equal to about 20 percent. Mixtures with greater than or equal to about 50 percent oxygen may also be used. As will be appreciated by one of skill in the art, the concentration of oxygen may affect the rate of the reaction. A preferred molecular oxygen containing gas is air.

Useful cobalt, manganese, bromide, zirconium, and hafnium sources are those sources which are soluble in acetic acid. Cobalt, manganese, zirconium and hafnium sources that may be used include the metals themselves or any of their salts, complexes or compounds. These include, but are not limited to, acetates, citrates, stearates, napthenates, acetylacetonates, benzoylacetonates, carbonates, sulfates, bromides, chlorides, fluorides, nitrates, hydroxides, alkoxides, nitrides, triflates, hydrates of the foregoing and mixtures of the foregoing. Preferably the cobalt in the cobalt source is in a +2 or +3 oxidation state. Preferably the manganese in the manganese source is in a +2 or +3 oxidation state. Examples of bromide sources include, but are not limited to, bromine, hydrogen bromide, a metal-bromide salt such as sodium bromide and organic bromides. Examples of organic bromides include tetrabromoethane, ethyl bromide, ethylene bromide, bromoform, xylyl bromide, xylylene bromide and mixtures comprising at least one of the organic bromides.

The mole percent of the cobalt, manganese, zirconium, hafnium, and bromide sources are based on the amount of chloro-ortho-xylene present at the beginning of the reaction. The cobalt source is generally present in amounts of about 0.25 to about 2 mol %. Preferably, the cobalt source is present in an amount of less than about 1.2 mol %. In addition, it is also preferable for the cobalt source to be present in an amount greater than or equal to about 0.5 mol %, and more preferably in an amount greater than or equal to about 0.8 mol %. It is particularly preferred for the amount of the cobalt source to be about 1 mol %.

The manganese source is present in amounts of about 0.1 to about 1 mol %. Preferably, the manganese source is present in an amount less than or equal to about 0.6 mol %. Additionally, it is also preferable for the manganese source to be present in an amount greater than or equal to about 0.3 mol %, more preferably greater than or equal to about 0.4 mol %. In a particularly preferred embodiment, the manganese source is present in an amount of about 0.5 mol %.

The bromide source is generally present in amounts of about 0.02 to about 0.05 mol %. Preferably, the amount of the bromide source is less than or equal to 0.04 mol %, and most preferably less than or equal to 0.03 mol %.

The zirconium source, hafnium source or mixture thereof is generally present in amounts of about 0.01 to about 0.1 mol %. Preferably, the zirconium source, hafnium source or mixture thereof is present in an amount less than or equal to about 0.06 mol %. Additionally it is also preferable for the zirconium source, hafnium source or mixture thereof to be present in an amount greater than or equal to about 0.03 mol %, more preferably greater than 0.04 mol %. In a particularly preferred embodiment, the zirconium source, hafnium source or mixture thereof is present in an amount of about 0.05 mol %.

In an exemplary process, the chlorophthalic acid may be produced by combining chloro-ortho-xylene, cobalt source; manganese source; bromide source, and zirconium source, hafnium source or mixture thereof in acetic acid in a reaction vessel. The reaction vessel is established at a pressure of greater than about 1600 Kpa and the desired reaction temperature, generally under an inert atmosphere such as nitrogen or argon. The temperature of the reaction is typically about 150° C. to about 170° C. The molecular oxygen containing gas is introduced to the reaction mixture and the flow of the molecular oxygen containing gas is maintained at a rate that creates an oxygen containing off gas with an oxygen concentration of less than 1 percent by volume. The oxygen concentration of the off gas may be determined by paramagnetic transduction oxygen analysis or other method known in the art. Useful flow rates are typically greater than or equal to 1.0 normal cubic meter ($m^3$)/hour per kilogram (kg) of chloro-ortho-xylene. A normal cubic meter is defined as cubic meter under standard temperature and pressure conditions. Preferably the reaction mixture, is agitated using standard methods such as mechanical stirring. The flow of the molecular oxygen containing gas continues until the off gas oxygen concentration exceeds about 3 percent by volume, indicating a slowing of the reaction. Once the off gas oxygen concentration exceeds about 3 percent by volume the flow of the molecular oxygen containing gas is modified so as to maintain the off gas oxygen concentration below about 5 percent by volume and the temperature of the reaction may be increased. It is preferable, however, for the temperature to remain below about 200° C. The flow of the molecular oxygen containing gas may be modified in several ways. The molecular oxygen containing gas may be diluted with an inert gas so as to decrease the oxygen concentration in the molecular oxygen containing gas, the flow rate of the molecular oxygen containing gas may be decreased, the source of the molecular oxygen containing gas may be changed so as to employ a molecular oxygen containing gas with a lower oxygen concentration or these methods may be combined so as to maintain the oxygen concentration of the off gas below about 5 percent by volume. The modified flow of the molecular oxygen containing gas is continued until at least about 90 percent of chloro-ortho-xylene has been converted to chlorophthalic acid, preferably until greater than about 95 percent has been converted. The amount of conversion achieved in the reaction can readily be determined through the use of gas chromatography, mass spectrometry or other methods known in the art. In our experience, the amount of time required to reach 90 percent conversion of chloro-ortho-xylene is about 3 to about 6 hours.

After the reaction reaches the desired level of completion, the chlorophthalic acid may be recovered as chlorophthalic acid or chlorophthalic anhydride. Many applications such as pharmaceutical applications and polymer synthesis require chlorophthalic acid and chlorophthalic anhydride with a high degree of purity. Such high degree of purity may be achieved by the method described herein. Impurities produced include chlorobenzoic acid, phthalic anhydride and chlorophthalide. In fact, chlorophthalide acid and chlorophthalic anhydride containing less than about 600 ppm of chlorophthalide (all chlorophthalide isomers), preferably less than about 500 ppm of chlorophthalide, and more preferably less than about 400 ppm of chlorophthalide is readily achievable. Additionally, chlorophthalic acid and chlorophthalic anhydride containing less than about 1% by weight of phthalic anhydride and chlorobenzoic acid may also be achieved. Chlorotoluic acids and dichlorophthalic acids are typically not detected.

Most of the acetic acid and water produced in the reaction can be removed by distillation at approximately atmospheric pressure, typically by heating to about 200° C. at 200 KPa. The acetic acid and water are removed as a vapor and condensed. The water may then be removed from the acetic acid and the acetic acid may be recycled. Some dehydration of the chlorophthalic acid to form chlorophthalic anhydride may occur simultaneously with the removal of acetic acid and water. Furthermore, the removal of acetic acid and water may be combined with dehydration to form a single step. Dehydration is typically done thermally by distillation under vacuum at an elevated temperature allowing dehydration and isolation of the chlorophthalic anhydride from any remaining acetic acid and water to occur simultaneously. Dehydration may also be carried out by other chemical reactions well known to those skilled in the art, such as treatment with acetic anhydride. After distillation the chlorophthalic anhydride is typically greater than about 98 percent pure and preferably greater than 99 percent pure. Chlorophthalic anhydrides of high purity are used in the synthesis of polyetherimide.

Polyetherimides are high heat engineering plastics having a variety of uses. One route for the synthesis of polyetherimides proceeds through a bis(4-chlorophthalimide) having the following structure (I)

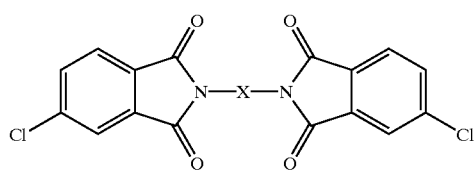
(I)

wherein X is a divalent alkylene, cycloalkylene, or arylene moiety. The bis(4-chlorophthalimide) wherein X is a 1,3-phenyl group (II) is particularly useful.

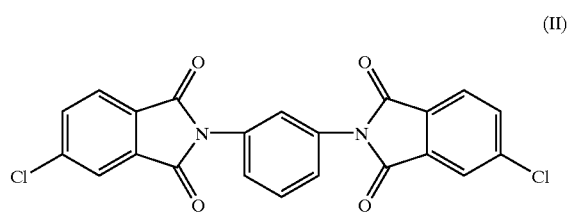
(II)

Bis(chlorophthalimide)s (I) and (II) are typically formed by the condensation of diamines, such as 1,3-diaminobenzene with anhydrides, such as 4-chlorophthalic anhydride (III):

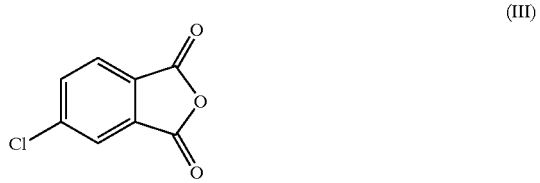
(III)

Polyetherimides may be synthesized by the reaction of the bis(chlorophthalimide) with an alkali metal salt of a dihydroxy substituted aromatic hydrocarbon in the presence or absence of phase transfer catalyst. Suitable phase transfer catalysts are disclosed in U.S. Pat. No. 5,229,482. Suitable dihydroxy substituted aromatic hydrocarbons include those having the formula (IV)

$$OH-A^2OH \quad (IV)$$

wherein $A^2$ is a divalent aromatic hydrocarbon radical. Suitable $A^2$ radicals include m-phenylene, p-phenylene, 4,4'-biphenylene, 4,4'-bi(3,5-dimethyl)phenylene, 2,3-bis(4-phenylene)propane and similar radicals such as those disclosed by name or formula in U.S. Pat. No. 4,217,438.

The $A^2$ radical preferably has the formula (V)

$$-A^3-Y-A^4- \quad (V)$$

wherein each of $A^3$ and $A^4$ is a monocyclic divalent aromatic hydrocarbon radical and Y is a bridging hydrocarbon radical in which one or two atoms separate $A^3$ from $A^4$. The free valence bonds in formula (V) are usually in the meta or para positions of $A^3$ and $A^4$ in relation to Y. $A^3$ and $A^4$ may be substituted phenylene or hydrocarbon-substituted derivative thereof, illustrative substituents (one or more) being alkyl and alkenyl. Unsubstituted phenylene radicals are preferred. Both $A^3$ and $A^4$ are preferably p-phenylene, although both may be o- or m-phenylene or one o- or m-phenylene and the other p-phenylene.

The bridging radical, Y, is one in which one or two atoms, preferably one, separate $A^3$ from $A^4$. Illustrative radicals of this type are methylene, cyclohexylmethylene, 2-(2,2,1)-bicycloheptylmethylene, ethylene, isopropylidene, neopentylidene, cyclohexylidene, and adamantylidene. The preferred radical of formula (IV) is 2,2-bis(4-phenylene)propane radical which is derived from bisphenol A and in which Y is isopropylidene and $A^3$ and $A^4$ are each p-phenylene.

It is clear to one of ordinary skill in the art that any impurities present in the chlorophthalic anhydride will be carried through to subsequent steps in the polyetherimide synthesis. The presence of significant levels of impurities in subsequent steps can interfere with polymerization and cause discoloration of the final product, polyetherimide.

The invention is further illustrated by the following non-limiting examples.

EXAMPLES 1–5

In a laboratory scale reactor 492 grams (g) (3.5 mol) of chloro-ortho-xylene (a mixture of about 30% 3-chloro-ortho-xylene and about 70% 4-chloro-ortho-xylene), 1925 g of glacial acetic acid, 8.7 g (1 mol %) of cobalt acetate tetrahydrate, 4.3 g (0.5 mol %) of manganese acetate tetrahydrate, 1.0 g (0.06 mol %) zirconium acetate solution, 4.3 g (1.5 mol %) sodium acetate and varying amounts of sodium bromide were combined. The reactor was filled with nitrogen, pressurized to 1900 KPa and heated to about 160° C. Air was then introduced to the reactor through a dip tube. Initially, the off gas oxygen concentration was greater than 0 but less than 1 percent. The reaction mixture was agitated throughout the reaction time. After about 3 hours the oxygen concentration of the off gas increased to greater than 3 percent. The flow of air was stopped. Air diluted with nitrogen so as to have an off gas oxygen concentration of about 5 percent was introduced to the reactor and the temperature of the reactor was increased to about 190° C. The flow of diluted air continued for about 1 to 3 hours. Chlorophthalic acid was determined to be present in an amount of 25 wt % based on the total weight of the reaction mixture. The majority of water formed by the reaction and the acetic acid were removed under atmospheric distillation. The chlorophthalic acid was dehydrated and any residual water and acetic acid were removed under heat and reduced pressure to form chlorophthalic anhydride. Chlorophthalic anhydride was separated from the catalyst by distillation under vacuum at distillation temperatures near 170° C. The isolated chlorophthalic acid was analyzed by gas chromatography. Results are shown in Table 1:

TABLE 1

| | | Amount of Chlorophthalides produced | |
|---|---|---|---|
| Example | NaBr mol % | wt % | ppm |
| 1* | 1.0 | 0.57 | 5700 |
| 2* | 0.29 | 0.25 | 2500 |
| 3* | 0.14 | 0.01 | 100 |
| 4 | 0.03 | 0.46 | 4600 |
| 5* | 0.014 | 2.35 | 23500 |

*comparative examples

As can be seen by examples 1–5, chlorophthalic anhydride with very small amounts of chlorophthalide may be produced on a laboratory scale, however the amount of bromide required is greater than 0.05 mol %.

EXAMPLES 6–10

In a pilot scale reaction 200 kilograms (kg) of chloro-ortho-xylene (a mixture of 3-chloro-ortho-xylene and 4-chloro-ortho-xylene), 780 kg of acetic acid, 3.5 kg (1.0 mol %) cobalt acetate tetrahydrate, 1.7.5 kg (0.5 mol %) manganese acetate tetrahydrate, 0.4 kg (0.05 mol %) zirconium acetate solution, 1.75 kg (1.5 mol %) sodium acetate and varying amounts of sodium bromide were combined. The amount of sodium bromide was varied by example as shown in Table 2. The reactor was filled with nitrogen, pressurized to 1900 Kpa and heated to about 160° C. Air was introduced to the reactor through a dip tube at a flow rate gradually increasing to 200 normal m³/h. Initially, the off gas oxygen concentration was greater than 0 but less than 1 percent. The reaction mixture was agitated throughout the reaction time. After about 1 hour, the reaction temperature was increased to 175° C. After about 3 hours the off gas oxygen concentration increased to greater than 3 percent. The air flow was stopped. Air diluted with nitrogen so as to have an off gas oxygen concentration of about 5 percent was introduced into the reactor and the temperature of the reactor was increased to 190° C. The flow of diluted air was continued for about 3 hours. Final weight of the reactor contents was consistent with high conversions of chloro-o-xylene based on the absorption of 3 moles of $O_2$ to generate the diacid and two moles of water. The majority of water formed by the reaction and the acetic acid were removed under atmospheric distillation. The chlorophthalic acid was dehydrated and any residual water and acetic acid were removed under heat and reduced pressure to form chlorophthalic anhydride. Chlorophthalic anhydride was separated from the catalyst by distillation under vacuum at distillation temperatures near 170° C. The isolated chlorophthalic acid was analyzed by gas chromatography. Results are shown in Table 2.

TABLE 2

| | NaBr | Amount of Chlorophthalides produced | |
|---|---|---|---|
| Example | mol % | (wt %) | ppm |
| 6* | 1.02 | 5.4 | 54000 |
| 7* | 0.14 | 0.24 | 2400 |
| 8* | 0.10 | 0.12 | 1200 |
| 9 | 0.03 | 0.02 | 200 |
| 10 | 0.02 | 0.03 | 300 |

*comparative examples

As can be seen in the preceding examples it is possible to produce chlorophthalic anhydride with very low levels of chlorophthalide in reactions on a large scale. The overall purity of the chlorophthalic acid produced in Examples 9 and 10 was greater than 98%.

EXAMPLE 11

In a laboratory scale reactor 40 grams (g) (284 millimole (mmol)) of chloro-ortho-xylene (a mixture of about 30% 3-chloro-ortho-xylene and about 70% 4-chloro-ortho-xylene), 160 g of glacial acetic acid, 567 milligrams (mg) (0.8 mol %) of cobalt acetate tetrahydrate, 349 mg (0.5 mol %) of manganese acetate tetrahydrate, 9.1 mg (0.06 mol %) zirconium acetate solution, and 91 mg of 30% solution by weight of hydrogen bromide in acetic acid were combined. The reactor was filled with nitrogen, pressurized to 1900 KPa and heated to about 160° C. Air was then introduced to the reactor through a dip tube. Initially, the off gas oxygen concentration was greater than 0 but less than 1 percent. The reaction mixture was agitated throughout the reaction time. After 1 hour at 160° C. the temperature was increased to about 175° C. After about 3 hours the oxygen concentration of the off gas increased to greater than 3 percent. The flow of air was stopped. Air diluted with nitrogen so as to have an off gas oxygen concentration of about 5 percent was introduced to the reactor and the temperature of the reactor was increased to about 190° C. The flow of diluted air continued for about 1 to 3 hours. The reaction mixture was analyzed by liquid chromatography (LC) and it was found that the chlorophthalic acid was formed with yield and impurity levels comparable to the results of Example 2.

Using the method for manufacture of chlorophthalic acid and anhydride described herein, the high yield synthesis of high purity chlorophthalic acid and anhydride is possible on a large scale employing hundreds of kilograms of chloro-ortho-xylene by liquid phase oxidation in the presence of about 0.25 to about 2 mol % of a cobalt source, about 0.1 to about 1 mol % of a manganese source, about 0.01 to about 0.1 mol % of a source of a metal selected from zirconium, hafnium and mixtures thereof, and about 0.02 to about 0.05 mol % of a bromide source of. Applicants have discovered that in large scale liquid phase oxidations employing chloro-ortho-xylene the amount of bromide can have a significant impact on the amount of impurities present in the final product. The use of decreasing molar percentages of bromide result in a product, either chlorophthalic acid or anhydride, with a decreased level of impurities such as chlorophthalide. While the reasons for this phenomenon are not clearly understood it is contemplated that even lower levels of bromide, molar percentages less than about 0.02, may be useful in producing high purity chlorophthalic acid or anhydride in even larger scale liquid phase oxidations such as those employing thousands of kilograms of chloro-ortho-xylene.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for the manufacture of chlorophthalic acid comprising: forming a reaction mixture comprising:
   a mixture of about 5 to about 3 parts by weight of acetic acid to 1 part by weight of a chloro-ortho xylene,
   about 0.25 to about 2 mole percent, based on said chloro-ortho-xylene, of a source of cobalt,
   about 0.1 to about 1 mole percent, based on said chloro-ortho-xylene, of a source of manganese,
   about 0.01 to about 0.1 mole percent, based on said chloro-ortho-xylene, of a source of a metal selected from zirconium, hafnium and mixtures thereof,
   about 0.02 to about 0.05 mole percent, based on said chloro-ortho-xylene, of a source of bromide;
   maintaining said reaction mixture at a pressure of at least about 1600 KPa and at a temperature of about 150° C. to about 170° C.;
   introducing a molecular oxygen containing gas to said reaction mixture at a rate of at least about 1.0 normal m$^3$ of gas/kg of chloro-ortho-xylene in said reaction mixture to create an oxygen containing off gas, wherein said off gas oxygen concentration is less than about one percent by volume of said off gas;
   maintaining said introduction of said molecular oxygen containing gas until the off gas oxygen concentration exceeds about 3 percent by volume of said off gas; and
   modifying the introduction of said molecular oxygen containing gas so as to maintain the off gas oxygen concentration at a concentration below about 5 percent by volume of said off gas and maintaining the modified introduction of said molecular oxygen containing gas for a time sufficient to provide at least about 90 percent conversion of said chloro-ortho-xylene to chlorophthalic acid.

2. The method of claim 1, wherein the molecular oxygen containing gas has an oxygen concentration of greater than or equal to about 6 percent oxygen.

3. The method of claim 1, wherein the molecular oxygen containing gas is air.

4. The method of claim 1, wherein the cobalt source, manganese source, zirconium or hafnium source, and bromide source are soluble in acetic acid.

5. The method of claim 4, wherein the cobalt source comprises cobalt acetate, cobalt napthenate, cobalt sulfate, cobalt acetylacetonate, cobalt benzoylacetonate, cobalt bromide, cobalt carbonate, cobalt chloride, cobalt fluoride, cobalt nitrate, cobalt stearate, or a hydrate of one of the foregoing cobalt compounds.

6. The method of claim 5, wherein the cobalt source comprises cobalt acetate or a hydrate of cobalt acetate.

7. The method of claim 4, wherein the manganese source comprises manganese acetate, manganese sulfate, manganese acetylacetonate, manganese bromide, manganese carbonate, manganese chloride, manganese fluoride, or manganese nitrate, or a hydrate of one of the foregoing manganese compounds.

8. The method of claim 7, wherein the manganese source comprises manganese acetate or a hydrate of manganese acetate.

9. The method of claim 4, wherein the zirconium source comprises zirconium acetate, zirconium sulfate, zirconium citrate, zirconium fluoride, zirconium hydroxide, zirconium alkoxide, zirconium chloride, zirconium bromide, zirconium acetylacetonate, or a hydrate of one of the foregoing zirconium compounds.

10. The method of claim 9, wherein the zirconium source comprises zirconium acetate or a hydrate of zirconium acetate.

11. The method of claim 4, wherein the source of hafnium comprises hafnium chloride, hafnium bromide, hafnium fluoride, hafnium iodide, hafnium nitride, hafnium sulfate, hafnium triflate, hafnium nitrate, or a hydrate of one of the foregoing hafnium compounds.

12. The method of claim 11, wherein the source of hafnium comprises hafnium chloride.

13. The method of claim 4, wherein the bromide source comprises bromine, hydrogen bromide, a metal-bromide salt or an organic bromide.

14. The method of claim 13, wherein the bromide source comprises sodium bromide.

15. The method of claim 13, wherein the bromide source comprises hydrogen bromide.

16. The method of claim 1, wherein the amount of the cobalt source is about 0.5 to about 1.2 mole percent, based on said chloro-ortho-xylene.

17. The method of claim 1, wherein the amount of the manganese source is about 0.3 to about 0.6 mole percent, based on said chloro-ortho-xylene.

18. The method of claim 1, wherein the amount of the source of zirconium or hafnium is about 0.03 to about 0.06 mole percent, based on said chloro-ortho-xylene.

19. The method of claim 1, wherein the amount of the source of bromide is less than or equal to about 0.04 mole percent, based on said chloro-ortho-xylene.

20. The method of claim 1, wherein the temperature is greater than or equal to 160° C.

21. The method of claim 1, wherein the conversion of said chloro-ortho-xylene to chlorophthalic acid is 95 percent or greater.

22. The method of claim 1, wherein said chloro-ortho-xylene comprises the 3-isomer, the 4-isomer or a mixture of 3- and 4-isomers.

23. The method of claim 1, further comprising increasing the temperature of the reaction mixture while maintaining the off gas oxygen concentration below about 5 percent by volume.

24. A method for the manufacture of chlorophthalic anhydride comprising:
forming a reaction mixture comprising:
a mixture of about 5 to about 3 parts by weight of acetic acid to 1 part by weight of a chloro-ortho-xylene,
about 0.25 to about 2 mole percent, based on said chloro-ortho-xylene, of a cobalt source,
about 0.1 to about 1 mole percent, based on said chloro-ortho-xylene, of a manganese source,
about 0.01 to about 0.1 mole percent, based on said chloro-ortho-xylene, of a source of metal selected from zirconium, hafnium and mixtures thereof,
about 0.02 to about 0.05 mole percent, based on said chloro-ortho-xylene, of a source of bromide;
maintaining said reaction mixture at a pressure of at least about 1600 KPa and at a temperature of about 150° C. to about 170° C.;
introducing a molecular oxygen containing gas to said reaction mixture at a rate of at least about 1.0 normal $m^3$ of gas/kg of chloro-ortho-xylene in said reaction mixture to create an oxygen containing off gas, wherein said off gas oxygen concentration is less than about one percent by volume of said off gas;
maintaining said introduction of said molecular oxygen containing gas until the off gas oxygen concentration exceeds about 3 percent by volume of said off gas; and
modifying the introduction of said molecular oxygen containing gas to maintain the off gas oxygen concentration at a concentration below about 5 percent by volume of said off gas and maintaining the modified introduction of said molecular oxygen containing gas for a time sufficient to provide at least about 90 percent conversion of said chloro-ortho-xylene to chlorophthalic acid;
removing the acetic acid and any water formed as a result of the reaction by distillation;
dehydrating said chlorophthalic acid to form chlorophthalic anhydride.

25. The method of claim 24, wherein the molecular oxygen containing gas has an oxygen concentration of greater than or equal to about 6 percent oxygen.

26. The method of claim 24, wherein the molecular oxygen containing gas is air.

27. The method of claim 24, wherein the cobalt source, manganese source, zirconium or hafnium source and bromide source are soluble in acetic acid.

28. The method of claim 27, wherein the cobalt source comprises cobalt acetate, cobalt napthenate, cobalt sulfate, cobalt acetylacetonate, cobalt benzoylacetonate, cobalt bromide, cobalt carbonate, cobalt chloride, cobalt fluoride, cobalt nitrate, cobalt stearate, or a hydrate of one of the foregoing cobalt compounds.

29. The method of claim 28, wherein the cobalt source comprises cobalt acetate or a hydrate of cobalt acetate.

30. The method of claim 27, wherein the manganese source comprises manganese acetate, manganese sulfate, manganese acetylacetonate, manganese bromide, manganese carbonate, manganese chloride, manganese fluoride, manganese nitrate, or a hydrate of one of the foregoing manganese compounds.

31. The method of claim 30, wherein the manganese source of comprises manganese acetate or a hydrate of one of the foregoing manganese compounds.

32. The method of claim 27, wherein the source of zirconium comprises zirconium acetate, zirconium sulfate, zirconium citrate, zirconium fluoride, zirconium hydroxide, zirconium alkoxide, zirconium chloride, zirconium bromide, zirconium acetylacetonate, or a hydrate of one of the foregoing zirconium compounds.

33. The method of claim 32, wherein the source of zirconium comprises zirconium acetate or a hydrate of zirconium acetate.

34. The method of claim 27, wherein the source of hafnium comprises hafnium chloride, hafnium bromide, hafnium fluoride, hafnium iodide, hafnium nitride, hafnium sulfate, hafnium triflate, hafnium nitrate, or a hydrate of one of the foregoing hafnium compounds.

35. The method of claim 34, wherein the source of hafnium comprises hafnium chloride.

36. The method of claim 27, wherein the source of bromide comprises bromine, hydrogen bromide, a metal-bromide salt or an organic bromide.

37. The method of claim 36, wherein the source of bromide comprises sodium bromide.

38. The method of claim 36, wherein the source of bromide comprises hydrogen bromide.

39. The method of claim 24, wherein the amount of the cobalt source is about 0.5 to about 1.2 mole percent, based on said chloro-ortho-xylene.

40. The method of claim 24, wherein the amount of the manganese source is about 0.3 to about 0.6 mole percent, based on said chloro-ortho-xylene.

41. The method of claim 24, wherein the amount of the source of zirconium or hafnium is about 0.03 to about 0.06 mole percent, based on said chloro-ortho-xylene.

42. The method of claim 24, wherein the amount of the source of bromide is less than or equal to about 0.04 mole percent, based on said chloro-ortho-xylene.

43. The method of claim 24, wherein the amount of the source of bromide is less than or equal to about 0.03 mole percent, based on said chloro-ortho-xylene.

44. The method of claim 24, wherein the temperature is greater than or equal to 160° C.

45. The method of claim 24, wherein the conversion of said chloro-ortho-xylene to chlorophthalic acid is 95 percent or greater.

46. The method of claim 24, wherein said chloro-ortho-xylene comprises the 3-isomer, the 4-isomer or a mixture of 3- and 4-isomers.

47. The method of claim 24, wherein said acetic acid is recycled to the reaction mixture.

48. The method of claim 24, further comprising increasing the temperature of the reaction mixture while maintaining the off gas oxygen concentration below about 5 percent by volume.

49. A method for the manufacture of chlorophthalic acid comprising: forming a reaction mixture comprising:
a mixture of about 5 to about 3 parts by weight of acetic acid to 1 part by weight of a chloro-ortho-xylene,
about 0.8 to about 1.2 mole percent, based on said chloro-ortho-xylene, of a cobalt source,
about 0.4 to about 0.6 mole percent, based on said chloro-ortho-xylene, of a manganese source,
about 0.04 to about 0.06 mole percent, based on said chloro-ortho-xylene, of a source of a metal selected from zirconium, hafnium and mixtures thereof,
less than about 0.04 mole percent, based on said chloro-ortho-xylene, of a source of bromide;
maintaining said reaction mixture at a pressure of at least about 1600 KPa and at a temperature of about 150° C. to about 170° C.;

introducing air to said reaction mixture at a rate of at least about 1.0 normal m$^3$ of gas/kg of chloro-ortho-xylene in said reaction mixture to create an oxygen containing off gas from said reaction mixture, wherein said off gas oxygen concentration is less than about one percent by volume of said off gas;

maintaining said introduction of said air until the off gas oxygen concentration exceeds about 3 percent by volume of said off gas; and modifying the introduction of said air so as to maintain the off gas oxygen concentration at a concentration below about 5 percent by volume of said off gas and maintaining the modified introduction of compressed air for a time sufficient to provide at least about 90 percent conversion of said chloro-ortho-xylene to chlorophthalic acid.

50. A method for the manufacture of chlorophthalic anhydride comprising: forming a reaction mixture comprising:

a mixture of about 5 to about 3 parts by weight of acetic acid to 1 part by weight of a chloro-ortho-xylene, about 0.8 to about 1.2 mole percent, based on said chloro-ortho-xylene, of cobalt acetate or cobalt acetate hydrate, about 0.4 to about 0.6 mole percent, based on said chloro-ortho-xylene, of manganese acetate or manganese acetate hydrate, about 0.04 to about 0.06 mole percent, based on said chloro-ortho-xylene, of zirconium acetate or zirconium acetate hydrate, less than about 0.04 mole percent, based on said chloro-ortho-xylene, of sodium bromide;

maintaining said reaction mixture at a pressure of at least about 1600 KPa and at a temperature of about 150° C. to about 170° C.;

introducing air to said reaction mixture at a rate of at least about 1.0 normal m$^3$ of gas/kg of chloro-ortho-xylene in said reaction mixture to create an oxygen containing off gas, wherein said off gas oxygen concentration is less than about one percent by volume of said off gas;

maintaining said introduction of said air until the off gas oxygen concentration exceeds about 3 percent by volume of said off gas;

modifying the introduction of the air so as to maintain the off gas oxygen concentration at a concentration below about 5 percent by volume of said off gas and maintaining the modified introduction of air for a time sufficient to provide at least about 90 percent conversion of said chloro-ortho-xylene to chlorophthalic acid;

removing the acetic acid and any water formed as a result of the reaction by distillation;

separating said water from said acetic acid and recycling said acetic acid; and dehydrating said chlorophthalic acid to form chlorophthalic anhydride.

51. A method for the manufacture of polyetherimide comprising: forming a reaction mixture comprising:

a mixture of about 5 to about 3 parts by weight of acetic acid to 1 part by weight of a chloro-ortho-xylene, about 0.25 to about 2 mole percent, based on said chloro-ortho-xylene, of a cobalt source, about 0.1 to about 1 mole percent, based on said chloro-ortho-xylene, of a manganese source, about 0.01 to about 0.1 mole percent, based on said chloro-ortho-xylene, of a source of a metal selected from zirconium, hafnium and mixtures thereof, about 0.02 to about 0.05 mole percent, based on said chloro-ortho-xylene, of a source of bromide;

maintaining said reaction mixture at a pressure of at least about 1600 KPa and at a temperature of about 150° C. to about 170° C.;

introducing a molecular oxygen containing gas to said reaction mixture at a rate of at least about 1.0 normal m$^3$ of gas/kg of chloro-ortho-xylene in said reaction mixture to create an oxygen containing off gas, wherein said off gas oxygen concentration is less than about one percent by volume of said off gas;

maintaining said introduction of said molecular oxygen containing gas until the off gas oxygen concentration exceeds about 3 percent by volume of said off gas;

modifying the introduction of the molecular oxygen containing gas so as to maintain the off gas oxygen concentration at a concentration below about 5 percent by volume of said off gas and maintaining the modified introduction of the molecular oxygen containing gas for a time sufficient to provide at least about 90 percent conversion of said chloro-ortho-xylene to chlorophthalic acid with less than about 200 parts per million (ppm) of chlorophthalide;

removing the acetic acid and any water formed as a result of the reaction by distillation;

dehydrating said chlorophthalic acid to form chlorophthalic anhydride;

reacting said chlorophthalic anhydride with 1,3-diaminobenzene to form bis(chlorophthalimide) (II)

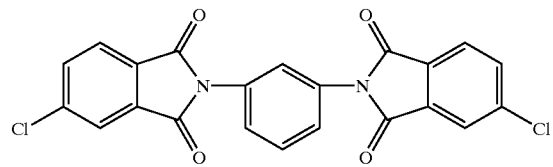

(II)

reacting bis(chlorophthalimide) (II) with an alkali metal salt of a dihydroxy substituted aromatic hydrocarbon having the formula (IV);

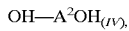

OH—A$^2$OH$_{(IV)}$, and wherein A$^2$ is a divalent aromatic hydrocarbon radical to form the polyetherimide.

* * * * *